United States Patent [19]
Kureshy et al.

[11] Patent Number: 5,141,871
[45] Date of Patent: Aug. 25, 1992

[54] FLUID DISPENSING SYSTEM WITH OPTICAL LOCATOR

[75] Inventors: Fareed Kureshy, Westwood; Ernest W. Long, Concord; Shailendra Singh, Sharon, all of Mass.

[73] Assignee: PB Diagnostic Systems, Inc., Westwood, Mass.

[21] Appl. No.: 521,364

[22] Filed: May 10, 1990

[51] Int. Cl.$^5$ .................. G01N 35/02; G01N 35/06
[52] U.S. Cl. ........................... 436/47; 436/49; 436/180; 422/64; 422/67; 356/375; 73/864.21; 73/864.211; 73/864.25
[58] Field of Search ........... 73/864.21, 864.24, 864.25; 356/375; 422/63–67, 100, , 68.1, 82.05, 82.08, 82.09; 436/44–49, 179–180

[56] References Cited

U.S. PATENT DOCUMENTS

| | | | |
|---|---|---|---|
| 3,699,348 | 10/1972 | Hocherl | 250/218 |
| 4,322,216 | 3/1982 | Lillig | 23/230 R |
| 4,344,768 | 8/1982 | Parker | 23/230 R |
| 4,420,254 | 12/1983 | Smeaton | 356/246 |
| 4,452,899 | 6/1984 | Alston | 436/46 |
| 4,478,094 | 10/1984 | Salomaa | 73/863.32 |
| 4,574,850 | 3/1986 | Davis | 141/9 |
| 4,586,546 | 5/1986 | Merci et al. | 141/2 |
| 4,846,003 | 7/1989 | Marquiss | 73/864 |
| 5,008,082 | 4/1991 | Shaw | 422/65 |

FOREIGN PATENT DOCUMENTS

| | | |
|---|---|---|
| 0311440 | 4/1989 | European Pat. Off. . |
| 0341438 | 11/1989 | European Pat. Off. . |
| 58-095262 | 6/1983 | Japan . |
| 61-26867 | 6/1986 | Japan . |

Primary Examiner—James C. Housel
Assistant Examiner—David Redding
Attorney, Agent, or Firm—Gaetano D. Maccarone

[57] ABSTRACT

There is described an analytical isntrument for the analysis of fluids such as biological fluids. The instrument includes a fluid dispensing system having a pipette for dispensing fluid test samples and test reagents to assay cartridges. An optical detection system provides a light beam which intercepts a downward travel path of the pipette prior to its reaching the dispense position. Measurement of the intensity of the light beam in conjunction with the position of the pipette enables a controller to indicate the presence or absence of a pipette tip. In addition, interception of the light beam by the pipette initiates a final approach sequence for the pipette to the dispense position above an assay cartridge by a predetermined increment of travel.

7 Claims, 5 Drawing Sheets

FLUID DISPENSING SYSTEM WITH OPTICAL LOCATOR

BACKGROUND OF THE INVENTION

This invention relates to a fluid dispensing system for use in automated analytical instruments and, more particularly, to such a system wherein an optical control system is utilized to precisely position the orifice of a pipette tip at a desired dispense position relative to an assay device.

Various types of chemical tests can be performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma or serum are tested to find evidence of disease, to monitor therapeutic drug levels, etc.

In the automated test instrument a sample of the test fluid is typically provided in a sample cup and all of the process steps including pipetting of the sample onto an assay test element, incubation and readout of the signal obtained are carried out automatically. All the process steps can be carried out while the assay test element is carried by a conveyor within a temperature controlled chamber. Further, in such instruments disposable pipette tips are typically used for the delivery of one fluid only and then discarded so as to avoid contamination which could lead to errors in the assay result. It is necessary, when dispensing sample fluid and/or test reagent(s) to the assay element that the orifice of the pipette tip be located at a predetermined, precisely controlled location above the assay element.

This requirement can be better understood from the following discussion of the typical manner in which a fluid dispensing system operates in a typical automated analytical instrument. The fluid dispensing system which includes a pipette is used to transfer sample fluid and/or test reagents from storage cups or wells within the instrument to the assay test element. The pipette includes a hollow tube or stem typically of metal, which is adapted to cooperate with a disposable pipette tip, which is typically made of a polymeric material. The disposable pipette tips are provided in a storage tray within the instrument. Initially, the pipette is advanced downwardly to secure a disposable tip by frictional contact. Thereafter, a predetermined amount of fluid is aspirated into the pipette tip and the tip is then moved automatically to a dispense position above an assay test element where a predetermined volume of the fluid is dispensed to the assay element. Upon completion of the dispense step the tip is discarded and a clean disposable tip is used for the next dispense step.

A problem can arise in the use of such a fluid dispense system due to the fact that each disposable tip is positioned on the metal stem of the pipette by a frictional fit. Since the polymeric materials from which disposable tips are typically made are flexible, there may be some variation from tip to tip as to the distance of the tip orifice from the metal stem of the pipette. Since, as mentioned previously, it is necessary to locate the pipette tip orifice at a predetermined, precisely controlled position above the assay element during the dispense steps, any variation in the positioning of the disposable tip on the pipette stem can result in an error in the desired positioning of the pipette tip which can lead to an error in the assay result.

Accordingly, it would be desirable to provide, in an analytical instrument which utilizes disposable tips in conjunction with a pipette for delivering fluids to an assay test element, the capability of determining the spatial location of the pipette tips during the dispense cycles so as to be able to arrange the orifice of the tips at a predetermined, precisely controlled position irrespective of the distance of the pipette tip orifice from the pipette stem. In addition, it would be advantageous to be able to determine whether the pipette has a disposable tip positioned thereon.

SUMMARY OF THE INVENTION

These and other objects and advantages are provided in accordance with the invention by an analytical instrument which employs a sensor comprised of a light source and a light detector to locate the tip position. The light beam is located in a plane immediately above the assay elements. The pipette can be positioned with some measure of accuracy by a servo system or a stepper motor, then final adjustment is made by use of the optical sensor. Thereupon, the fluid is discharged and the pipette prepared for reuse. Reuse is accomplished by removal of the used disposable tip and replacement with a new disposable tip. The used tip is removed by moving the pipette into a tip extractor fixture which envelops a lip of the tip. Thereupon, the stem of the pipitte is raised to withdraw the used tip which falls off into a collection tray.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
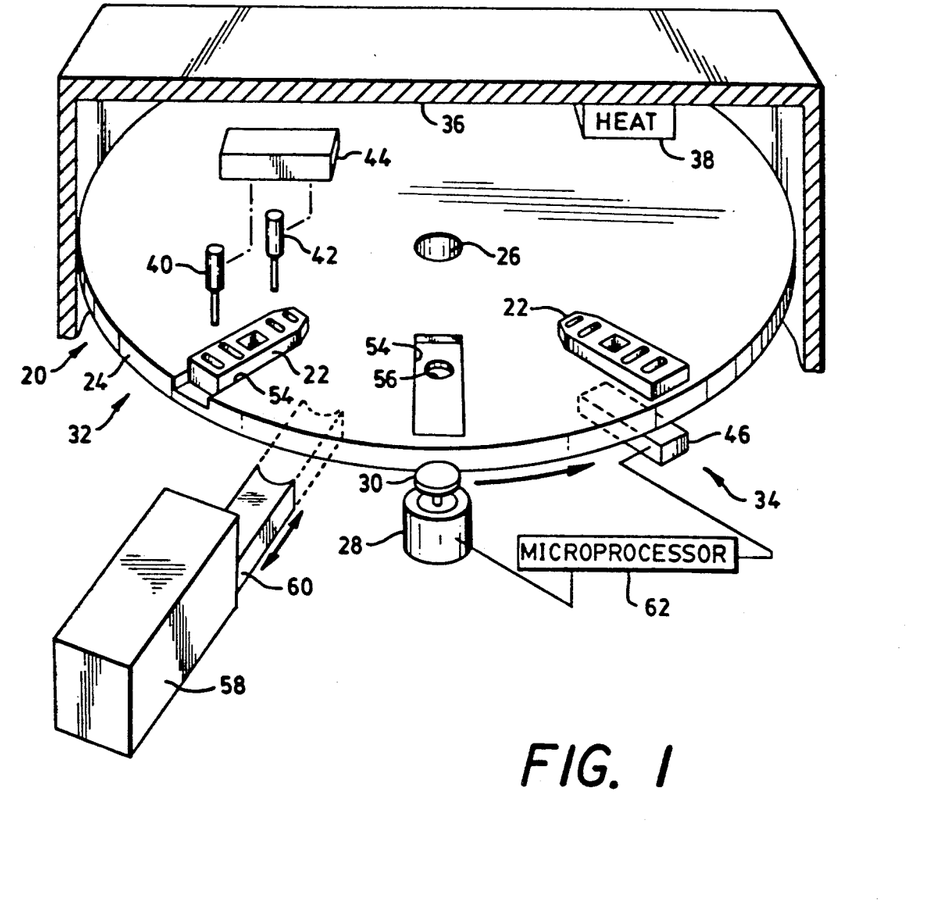
FIG. 1 is a stylized view, partially diagrammatic, of an analytical instrument including assay test cartridges and a carousel for moving the cartridges from one work station to another.

In FIG. 1, there is shown an analytical instrument 20 which provides automatically a sequence of process steps to accomplish an assay of a test sample. A plurality of cartridges 22 are employed within the instrument 20 to increase the throughput rate, one process step being carried out with one cartridge concurrently with the performance of other process steps with other cartridges. The cartridges 22 are illustrated with respect to a preferred embodiment thereof which includes one or more chambers in the housing. Such chambers may be configured as wells, or reservoirs, for the storage and/or mixing of fluids which are used in the assay procedure or the chambers may culminate in an opening to permit fluids to be provided to a reaction zone within the cartridge. The chambers are formed integrally within the housing of the cartridge. The analytical instrument 20 includes a turntable or carousel 24 which is rotated about an axle 26 by a motor 28. By way of example, the motor 28 may be mechanically coupled to the carousel 24 by a gear 30 or by a belt drive (not shown). The carousel 24 carries the cartridges 22 from one work station to another work station, two such work stations 32 and 34 being shown, by way of example, in FIG. 1. The carousel 24 rotates within a temperature controlled chamber 36 having a heater 38 for maintaining a desired temperature at the various work stations so as to allow for a process step of incubation.

Work station 32 is a pipetting station whereat sample fluid and any other required fluid test reagent(s) are delivered to the assay cartridges 22. By way of example, there are shown two pipettes 40 and 42. The pipettes, 40 and 42, are positioned and operated by a pipette mechanism 44 mechanically connected to the pipettes 40 and 42, as indicated by dashed lines.

During the assay procedure, as a result of the reaction(s) and interaction(s) between the sample fluid and the test reagent(s) which take place, a detectable change is effected corresponding to the presence of an analyte or component of interest in the sample fluid. The detectable change may be a color change which may be read spectrophotometrically such as with a densitometer or, in an assay method based on fluorescent-labeled biologically active species or one which involves the generation of a fluorescent species as a result of a reaction between test reagents, a fluorescent output signal can be generated and read spectrofluorometrically. Such detectable changes may be read from above or below the assay cartridge. At work station 34 there is shown by way of example a fluorometer 46 for irradiating the reaction zone within the assay cartridge and for measuring the fluorescence emitted from the fluorescent species present therein.

The carousel 24 may be arranged so as to accomodate varying numbers of assay cartridges 22. Each position, or berth 54 for holding an assay cartridge is provided in this embodiment with a small aperture 56 to allow the irradiating illumination to reach the reaction zone in the assay cartridge and to permit the reflected fluorescent emissions to be collected and measured. Also shown is an injector 58 for inserting a cartridge 22 in an empty berth 54, the injector 58 having an arm 60 for gripping a cartridge 22 during the insertion operation. The injector 58 also serves to extract a cartridge from a berth 54 by use of the arm 60 upon completion of a test procedure. Operation of the motor 28, the pipette mechanism 44, the fluorometer 46 and the injector 58 are synchronized by means of a microprocessor 62.

Figure 2:
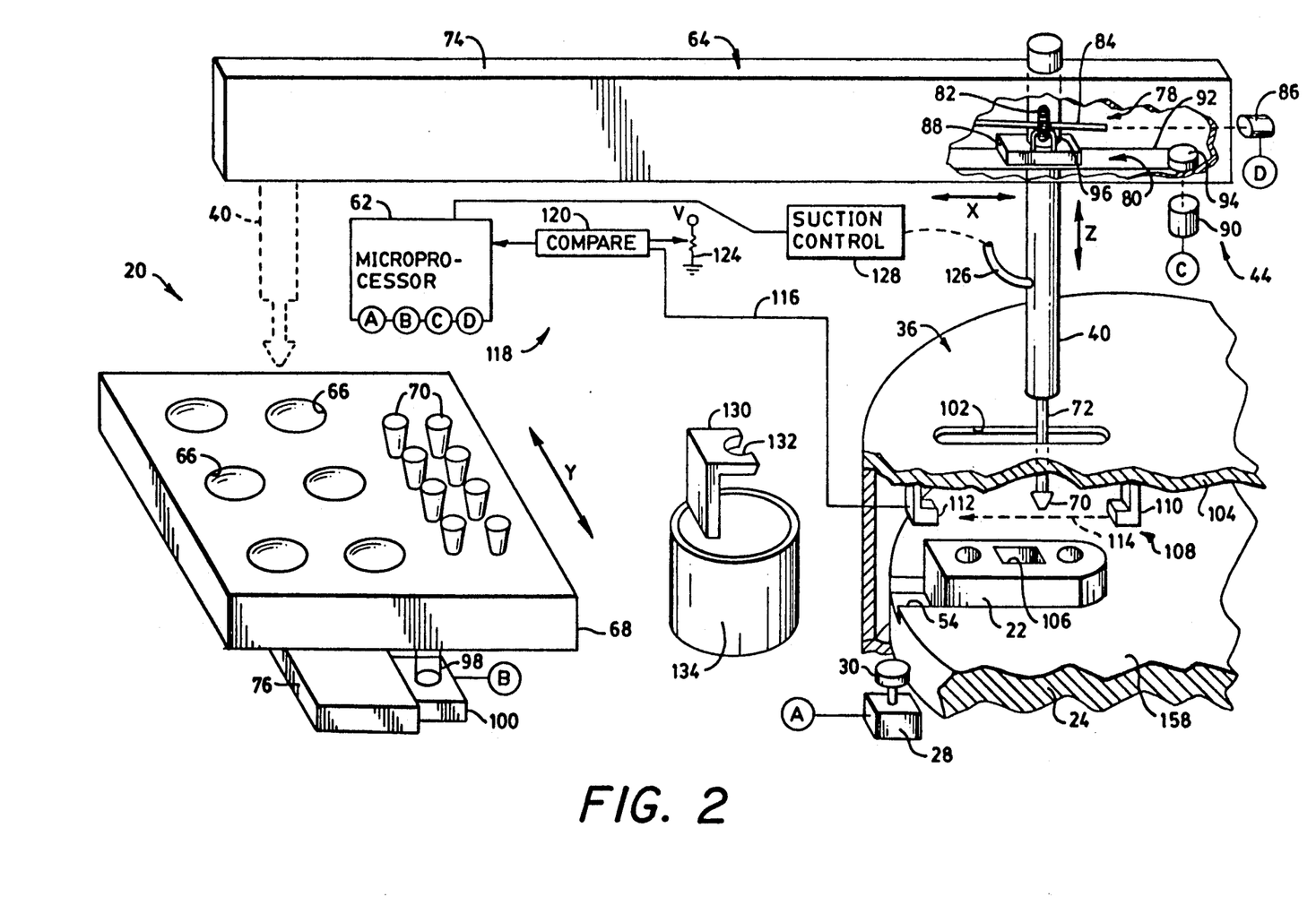
FIG. 2 is a stylized view, partially diagrammatic of a pipette transport for moving the pipette between a supply of disposable tips, reagent reservoirs, and compartments of an assay cartridge, the figure showing also an optical detection system for sensing the location of a tip of the pipette.

FIG. 2 illustrates detail in the construction of the pipette mechanism 44 of FIG. 1. To facilitate description of the invention, the pipette mechanism 44 will be described hereinafter as having a pipette transport 64 operative with only one of the pipettes, namely, the pipette 40. The transport 64 provides for relative movement, in two dimensions, between the pipette 40 and a set of reservoirs 66 located at a distance from the assay cartridge 22, the reservoirs 66 serving to store sample fluids or other fluid reagents useful in the assays carried out by the instrument 20. The reservoirs 66 are located on a movable table 68 which also holds a set of disposable tips 70 which are to be affixed to a stem 72 of the pipette 40. With reference to an X-Y-Z coordinate axis system, the pipette 40 is translatable in the X direction along a box beam 74 of the transport 64, and the table 68 is translatable in the Y direction by riding along a rail 76 of the transport 64. A vertical drive 78 is located within the beam 74 and serves to raise and to lower the pipette 40 in the Z direction.

A horizontal drive 80 located within the box beam 74 drives the pipette in the X direction. The vertical drive 78 and the horizontal drive 80 are of conventional design, and are indicated in simplified fashion in FIG. 2. In simplified fashion, the vertical drive 78 may be described as comprising a wheel 82 slideably mounted to a spline shaft 84 which, alternatively, may have a square cross section. The shaft 84 is rotated by a motor 86. The horizontal drive 80 includes a base 88 which slides in the X direction along the beam 74 in response to rotation of a motor 90. The motor 90 drives a belt 92 through a pulley 94, the belt 92 being connected to the base 88 for translating the base 88 upon rotation of the pulley 94 by the motor 90. A fixture 96 upstanding from the base 88 slides the wheel 82 along the shaft 84 upon movement of the base 88 so that the wheel 82 stays in fixed position relative to the base 88. The pipette 40 passes through the base 88 so as to be translated in the X direction by the base 88. The wheel 82 is mechanically connected to the pipette 40, as by gear teeth on the wheel 82, or by means of a belt drive (not shown). The mechanical connection of the wheel 82 to the pipette 40 provides for a translation of the pipette 40 in the Z direction upon rotation of the wheel 82 by the motor 86. The belt drive 98 may be employed, similarly, for driving the table 68 in the Y direction in response to rotation of a motor 100 affixed to the rail 76.

As noted above in the description of the analytical instrument of FIG. 1, the motor 28 is under control of the microprocessor 62. Similarly, the motors 100, 90, and 86 are also under control of the microprocessor 62. Connections of the motors 28, 100, 90, and 86 are indicated in FIG. 2 by terminals A, B. C, and D, respectively. Thereby, movement of the pipette 40 can be synchronized with a positioning of the cartridge 22 by the carousel 24 to a location directly beneath the beam 74. In order to provide access to the cartridge 22 by the pipette 44, a slot 102 is provided in the top wall 104 of the temperature controlled chamber 36. The slot 102 is parallel to the beam 74. The location of the slot 102 relative to the beam 74 permits the stem 72 of the pipette 40 to be lowered through the slot 102 selectively above a desired compartment of a plurality of compartments 106 of the cartridge 22. The length of the slot 102 is commensurate with the length of the cartridge 22 to permit displacement of the stem 72 in the X direction for alignment with a selected one of the compartments 106. The slot 102 is relatively narrow, and has a width large enough to clear the stem 72 and the tip 70 mounted on the distal end of the stem 72. With respect to the overall dimension of the temperature controlled chamber 36, the area occupied by the slot 102 is sufficiently small to preclude any significant amount of air flow between the interior and the exterior of the temperature controlled chamber 36. Thereby, the slot 102 has no more than a negligible effect in the control of the temperature of the chamber, which temperature is controlled by the heater 38 (FIG. 1).

In accordance with a feature of the invention, an optical detection system 108 is provided to signal the microprocessor 62 when the tip 70 of the pipette 40 has advanced in the downward direction to a predetermined distance from the selected compartment 106. The detection system 108 comprises a source 110 of light which, by way of example, may be a semiconductor diode which emits infrared radiation. The detection system 108 also comprises a detector 112, the light being indicated by a beam 114. The detector 112, which may comprise a semiconductor photodiode, modulates an electric current along line 116 in response to light of the beam 114 incident upon the detector 112.

The detection system 108 includes electrical comparison circuitry 118 for measuring the magnitude of the current on line 116. By way of example in the construction of the circuitry 118, the circuitry 118 comprises a comparator 120 and a resistive voltage divider 124 providing a reference voltage to the comparator 120. The divider 124 is shown to comprise two potentiometer for allowing manual adjustment of the reference voltage for initial alignment of the detection system 108. The alignment provides for selection of a comparator reference voltage in accordance with the degree of optical transparency of the tip 70.

In the operation of the detection system 108, the full strength of the light beam 114 is incident upon the detector 112 in the absence of the pipette 40. By way of example, the pipette 40 may be at the location of one of the reservoirs 66, as indicated in phantom view of the pipette. During maximum intensity of the received optical signal at the detector 112, a maximum current and voltage appear on line 116. During descent of the pipette 40, the tip 70 interrupts the light beam 114. The line 116 is connected to the input terminal of the comparator 120 and, accordingly, the comparator 120 outputs a logic-1 signal to the microprocessor 62 under conditions of maximum illumination of the detector 112, as occurs prior to interruption of the light beam 114 by the pipette 40. Interruption of the light beam 114 greatly reduces the intensity of light received at the detector 112. The extent of the interruption of the light depends on the degree of the transparency of the tip 70. The tip 70 is preferably fabricated of a polymeric material which is translucent so as to reduce the intensity of the light without casting a complete shadow upon the detector 112.

The voltage reference levels of the divider 124 are set such that the amount of light transmitted by a tip is sufficient to activate the comparator 120 to output a logic-1 signal indicating a low, L, level of light received at the detector 112. In the event that the light beam 114 is interrupted by a tip 70, then the intensity of light received by the detector 112 is too low to activate the comparator 120 with the result that the comparator outputs logic-0. Thus, there is a 1-bit outputted by the comparison circuitry 118 designating the status and location of the tip 70 as the tip 70 advances along a path of travel in the Z direction to a selected compartment 106 of the cartridge 22.

Fluid reagent is drawn into the pipette tip 70 and expelled from the tip 70 by vacuum pressure delivered to the pipette 40 by a suction tube 126 under control of a suction control unit 128. The tube 126 is flexible and of sufficient length to connect the suction control unit 128 with the pipette 40 at all locations of the pipette 40. The control unit 128 is connected to the microprocessor 62 which commands the control unit 128 to apply vacuum for inducting liquid, and for releasing vacuum and applying positive pressure, if necessary, to expel the fluid reagent. Aspiration of fluid is carried out from a selected one of the reservoirs 66. Expelling of the fluid reagent is accomplished only when the tip 70 is in the position for dispensing the fluid to the selected one of the compartments 106 in the designated cartridge 22. It is noted also that aspiration of fluid reagent can be accomplished at one of the compartments 106 of the cartridge 22 to be dispensed in another of the compartments 106. In this respect, a reservoir for storage of liquid reagent can be located directly within the cartridge 22 or remote from the cartridge 22, as at the table 68. The location of the various reservoirs 66 of the table 68 are stored in a memory of the microprocessor 62. This enables the microprocessor 62 to move the table 68 to a specific address in the Y direction, and to move the pipette 40 to a specific address in the X direction, the X and the Y components of the address fully identifying the requisite one of the reservoirs 66. In similar fashion, the microprocessor 62 stores locations of the available tips 70 held by the table 68 so that successive ones of the tips 70 can be selected for affixation to the stem 72.

The transport 64 is operative in the process of affixing a tip 70 to the stem 72 of a pipette 40, and in the detachment of the tip 70 from the stem 72. The procedure begins by a lifting of the pipette 40 so that the tip 70 clears the slot 102. The pipette 40 is then free to move along the beam 74 to an extractor 130. The extractor 130 has a semicircular channel 132 cut out in the edge of a horizontal portion of the extractor 130, the channel 132 having a diameter large enough to permit clearance of the stem 72 by the channel 132, but small enough to permit engagement of the channel 132 with the tip 70. Under commands of the microprocessor 62, the pipette is brought towards the extractor 130 with the tip 70 being below the channel 132. The stem 72 enters the channel 132 after which the pipette 40 is raised to engage the tip 70 With the extractor 130. The tip 70 remains stationary as the stem 72 lifts out of the tip 70. Thereupon, the tip 70 falls into a bin 134 for collection of used tips 70. It is advisable to employ the extractor 130 at the beginning of operation of the test system 20 to ensure that the stem 72 is free for reception of a new tip 70.

After ensuring that the stem 72 is free for reception of a tip 70, the pipette 40 is brought, by displacement in the X direction, to a location above the table 68, whereupon the table 68 is translated in the Y direction to bring the stem 72 above and in registration with a selected tip 70 held by the table 68. The pipette 40 then advances downward to make frictional contact with the interior surface of the tip 70. Thereupon, the pipette is raised, and the tip is retained on the distal end of the stem 72 by friction forces.

Figures 3, 4:
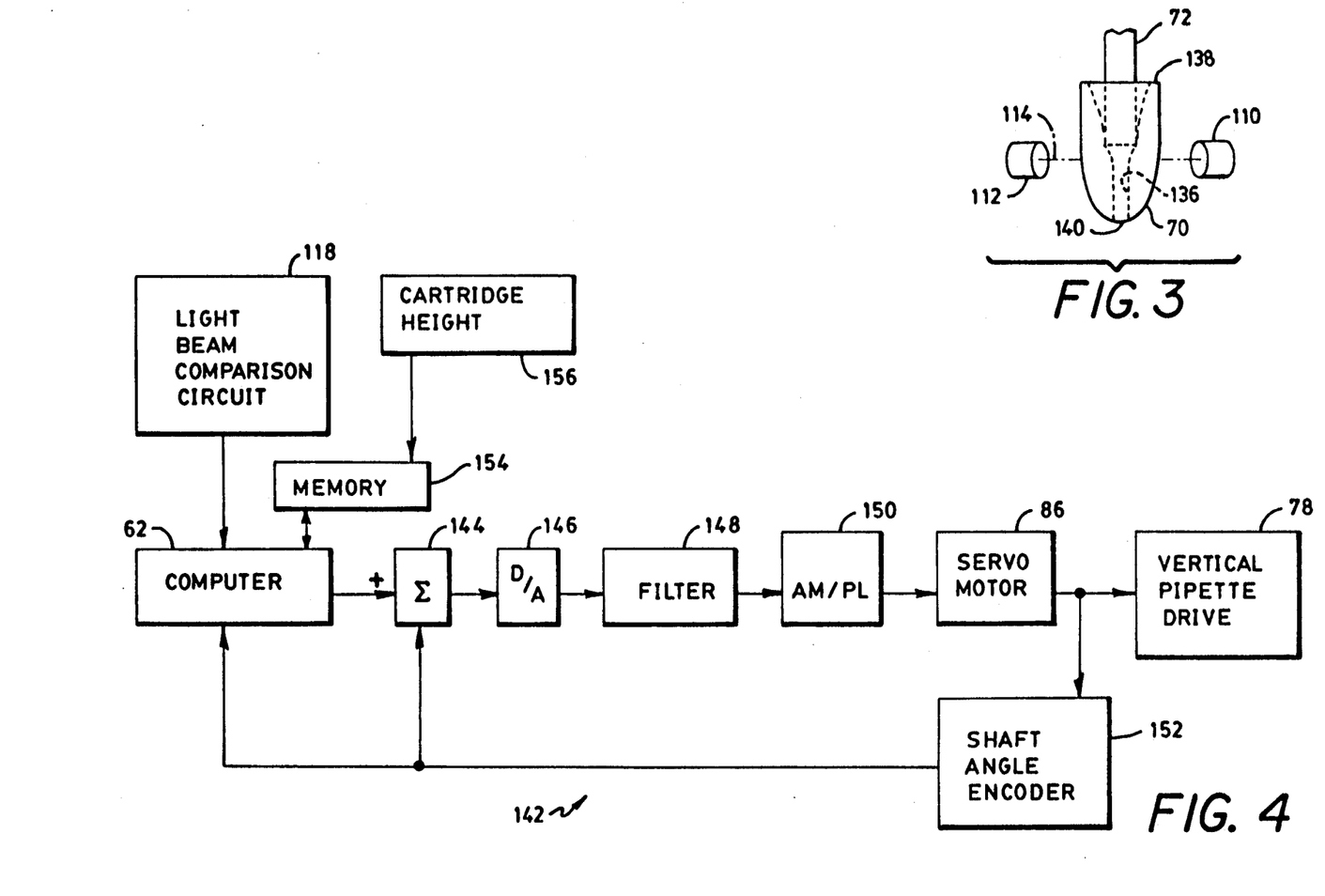
FIG. 3 is an enlarged fragmentary view of a disposable tip of the pipette within a light beam of the optical detection system.
FIG. 4 is a block diagram showing a servo control loop of the pipette transport operative with a microprocessor for positioning the pipette within the vertical direction.

With reference also to FIG. 3, the distal end of the stem 72 is shown making frictional contact with the surface of a channel 136 of the tip 70. The channel 136 extends along a central longitudinal axis of the tip 70 from one end of the tip to the opposite end of the tip. The channel 136 has a circular cross-sectional shape of varying diameter, the diameter being larger at the top end 138 than at the bottom end 140. As the stem 72 advances downwardly into the channel 136, constriction of the channel 136 produces frictional forces which tighten the tip 70 upon the stem 72. These frictional forces are sufficient to ensure a secure attachment of the tip 70 to the stem 72 during transfer of liquid reagent during test procedures of the system 20. However, the frictional forces are sufficiently small to permit the extractor 130 to slide the tip 70 off of the stem 72 upon completion of a transfer of liquid reagent.

With respect to the practice of the invention, it is noted that the manner of affixing the stem 72 to the tip 70 provides substantial uniformity in the locations of successive tips 70 upon the stem 72. However, in view of the flexibility of the polymeric material of the tip 70 brought about by contact with the relatively rigid tube of the stem 72, and in view of some variation in frictional forces among the tips 70, it has been found that there is slight variation among the locations of the orifices 140 of the tips 70 relative to the distal end of the stem 72. This variation is sufficient to serve as a source of inaccuracy to the dispensing of liquid in the compartments 106 of the cartridge 22. The invention automatically corrects for these variations in tip location by sensing the location of the orifices 140 of the tip 70 by means of the light beam 114. The procedure of the invention for correcting for the variations in tip location is explained further with reference to the diagram of FIG. 4 and the flow charts of FIGS. 5-6.

FIG. 4 shows the feedback circuit 142 for interconnecting the microprocessor 62 with the servo motor 86 for operation of the vertical pipette drive 78 disclosed in FIG. 2. As shown in FIG. 4, the circuit 142 includes a summer 144, a digital-to-analog converter 146, a filter 148, an amplifier 150, a shaft angle encoder 152, a memory 154 of the computer 62, and an entry device 156, such as a keyboard, for entering data into the memory 154.

In operation, for lowering the pipette 40 towards the cartridge 22 (FIG. 2), the microprocessor 62 successively enters new locations on the path of travel of the pipette 40 in the Z direction. Location signals of the microprocessor 62 are applied to one input terminal of the summer 144. The present location of the tip 70, as estimated by the encoder 152 is applied to a second input terminal of the summer 144 to be subtracted from the value input at the first terminal of the summer 144. It is noted that the encoder 152 provides an accurate value of the location of the pipette stem 72, but not of the tip 70, because the position of the tip 70 relative to the stem 72 varies from tip to tip because of the frictional fit explained above. Therefore, a value of shaft angle outputted by the encoder 152 can be taken only as an estimate of the true position of the tip 70.

The signals outputted by the encoder 152 and by the microprocessor 62 are formatted digitally. The summer 144 forms the difference of these two signals and applies the difference to the converter 146 for converting the difference from a digitally formatted signal to an analog signal. The analog signal outputted by the converter 146 may be regarded as the loop error signal of the feedback circuit 142. The loop error signal is filtered by the filter 148 which, in accordance with the usual practice in the construction of the feedback loops, may be a low-pass filter, and may include a lead-lag filter component. The filter 148 provides stability to the feedback loop. An output signal of the filter 148 is amplified by the amplifier 150, and is applied to the servo motor 86. The loop gain and bandwidth, as established by the amplifier 150 and the filter 148, in conjunction with the motor 86 determines the dynamic response of the loop in a manner well known in the design of servomechanisms. The motor 86 rotates towards the rotational position commanded by the microprocessor 62. As the motor 86 rotates, the vertical drive 78 lowers the pipette 40.

By way of alternative embodiment in the construction of the feedback circuit of FIG. 4, it is noted that the functions of the summer 144 and the filter 148 can be accomplished directly within the microprocessor 62 by suitable programming of the microprocessor 62. In such a case, the microprocessor 62 outputs the error signal via the converter 146 directly to the amplifier 150 for driving the motor 86. Also, if desired, the servo motor 86 can be replaced with a stepping motor (not shown) which operates in response to digital pulses directing incremental rotational displacement of a rotor of the motor. In such a case, summer 144, converter 146, filter 148, amplifier 150, and shaft angle decoder 152 would not be required, and the microprocessor 62 would be programmed to output well-known stepping-motor control pulses for driving the motor. It is to be understood that any one of these configurations of feedback loop can be employed to operate the vertical pipette drive 78, the configuration of FIG. 4 having been shown to facilitate the teaching of the practice of the invention.

With respect to the circuit shown in FIG. 4, the microprocessor 62 continues to input further values of position along the path traveled by the pipette 40 until the light-beam comparison circuit 118 signals the microprocessor 62 of a break in the light beam. The location of the tip 70 is now known accurately by virtue of contact of the tip 70 with the light beam 114. The pipette 40 now travels through an additional distance to bring the tip 70 into the dispensing position relative to the cartridge 22. The value of the additional distance of positional travel is based on data stored in the memory 154. The microprocessor 62 reads the memory 154 to obtain the travel data. A person operating the analytical instrument 20 provides the requisite data on additional travel based on a knowledge of the configuration of the cartridge 22, particularly the height of the cartridge 156 relative to a top surface 158 of the carousel 24. This height data is entered via the entry device 156 in the memory 154.

Figure 6:
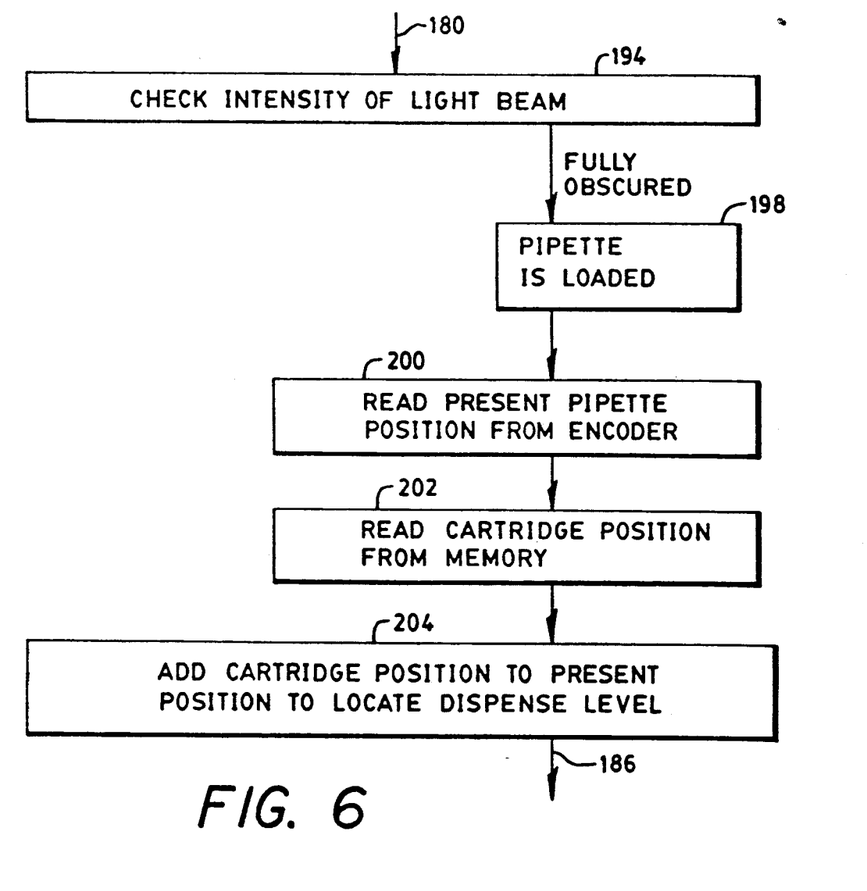
FIG. 6 shows details in a block of the chart of FIG. 5 relating to the computation of additional pipette travel, including a safety check to insure that a pipette is present on the pipette barrel.
Figure 7:
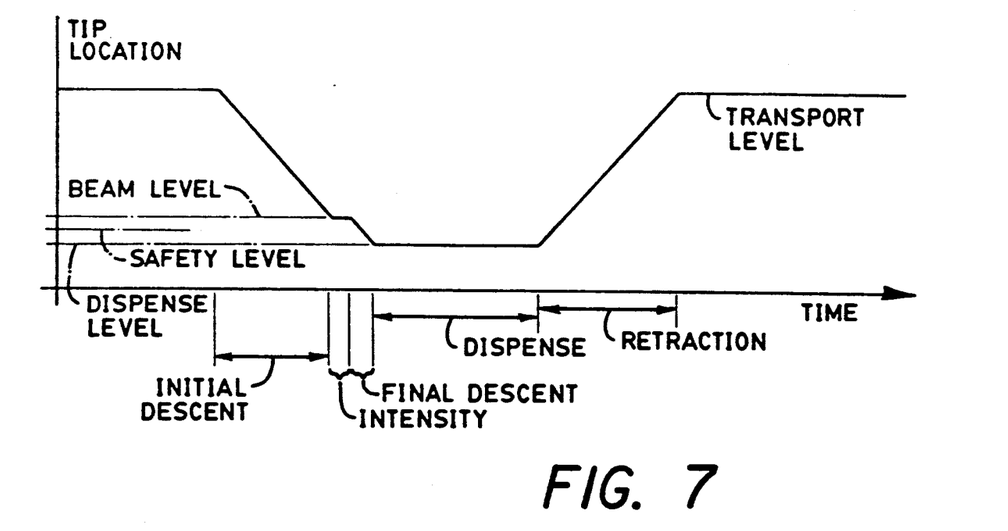
FIG. 7 is a timing diagram showing vertical movement of the pipette.

The operation of the feedback circuit 142 may be explained further with reference to FIG. 2 and with reference to the timing diagram of FIG. 7. Prior to the lowering of the pipette 40, the tip 70 is at a sufficiently high elevation to permit transporting the pipette 40 in the X direction between the carousel 24 and the table 68. This is referred to in FIG. 7 as the transport level. The pipette 40 then undergoes its initial descent during an interval of time identified in FIG. 7. The initial descent interval ends with the breaking of the light beam 114. Thereupon, there is the final interval of descent in which the pipette 40 descends the additional distance. This brings the pipette tip to the dispense level indicated in FIG. 7. After completion of a dispensing interval of time, the feedback circuit 142 raises the pipette 40 back to the transport level during a retraction interval shown in FIG. 7. Also shown in FIG. 7 is a safety level which will be described with reference to the flow charts of FIGS. 5-6.

Figure 5:
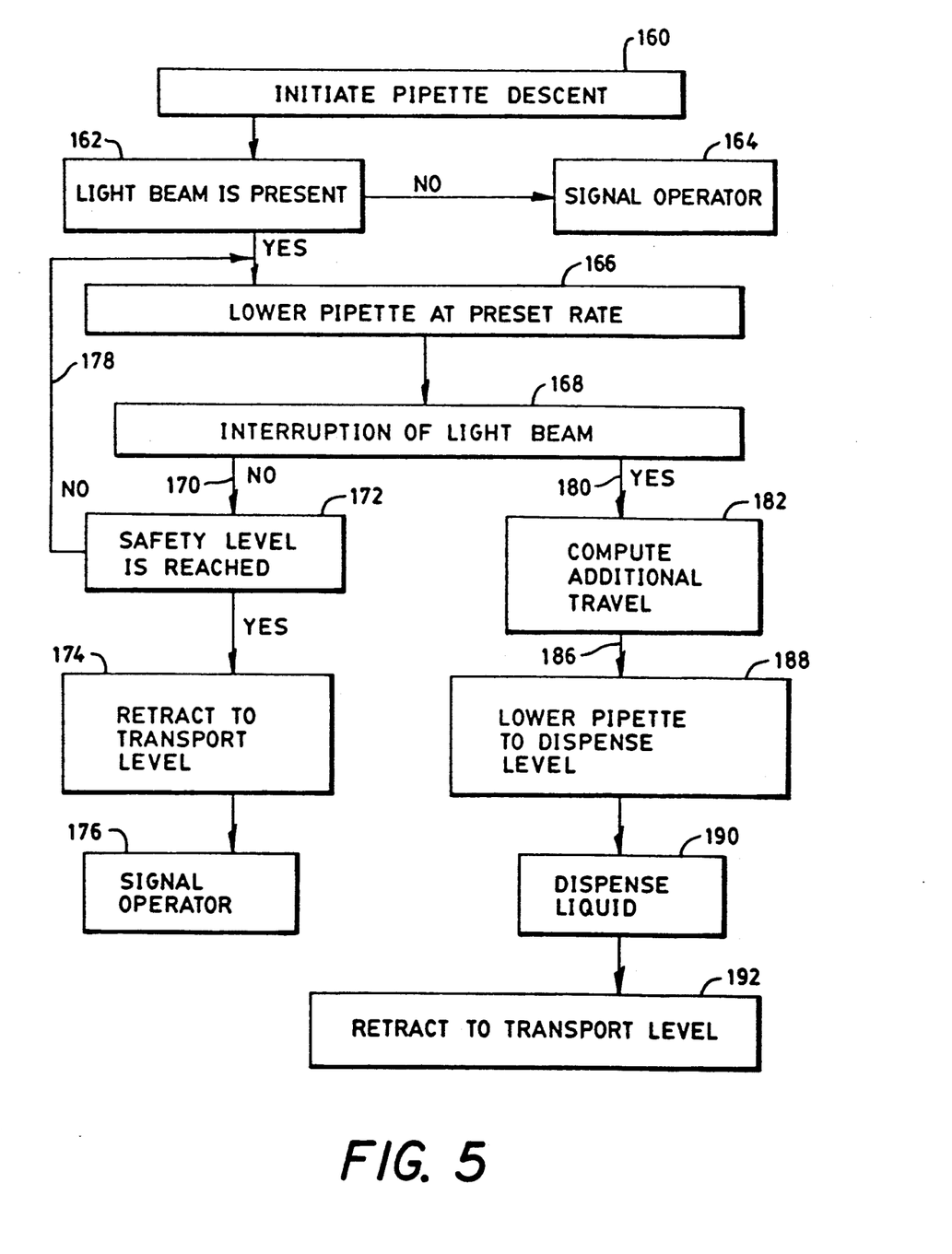
FIG. 5 is a flow chart showing operation of the microprocessor.

With reference to FIG. 5, the inventive feature of lowering the pipette to the cartridge 22 while compensating for variations in positions of the tip 70 is explained with reference to a flow chart. The flow chart describes operation of the microprocessor 62 of FIG. 2 for operating the vertical pipette drive 78 (FIGS. 2 and 4) for lowering the pipette 40 to dispense liquid reagent in a compartment 106 of the cartridge 22. Initiation of the pipette descent toward the cartridge 22 occurs at block 160. At block 162, the determination is made as to whether the light beam 114 (FIG. 2) is present. The microprocessor 62 determines the presence of the light beam by examination of the high and low signals outputted by the comparison circuitry 118. Since the pipette 40 is in an elevated position, there is no blockage of the light beam 114 and, accordingly, the light beam 114 should be present and the comparator 120 should be outputting the logic-1 signal indicating full intensity of the light beam 114. If the beam is not present, then, at block 164, a person operating the analytical instrument 20 is signaled to correct an apparent fault in the instrument.

If the light beam is present, the procedure advances to block 166 wherein the microprocessor 62 directs the lowering of the pipette 40 in the manner described above with reference to FIG. 4. Therein, the microprocessor 62 continually inputs new positions along the path of travel of the pipette 40 at a rate commensurate with the dynamic response of the feedback loop 142. Periodically, during the lowering of the pipette 40, the microprocessor 62 observes output signals of the comparison circuitry 118 to determine whether there has been an interruption of the light beam 114, this determination being performed at block 168.

Assuming that no interruption of the light beam 114 by the pipette 40 has occurred, then operation proceeds along line 170 to block 172 to determine whether the safety level (shown in FIG. 7), has been reached. There is the possibility of a system malfunction wherein the stem 72 of the pipette 40 has failed to secure the tip 70 at the table 68. This could occur for a variety of reasons, such as operator negligence in filling the table 68 with the set of tips 70, or the possibility of a cracked tip which fails to provide adequate friction for securing the tip to the stem 72. Since the shaft angle encoder 152 (FIG. 4) continually outputs position data to the microprocessor 62, the microprocessor 62 has knowledge of the location of the distal end of the stem 72. As the distal end of the stem 72 approaches the vicinity of the light beam 114, there should be an interruption of the beam 114 by the tip 70, assuming the tip 70 is present. The safety level is the lowest point at which the microprocessor 62 will allow the stem 72 to drop without interruption of the beam 114. If the safety level is reached, then the microprocessor 62 concludes that the tip 70 is absent, and operation proceeds to block 174 wherein the microprocessor 62 orders retraction of the pipette 40 to the transport level. As noted hereinabove, at the transport level, the pipette 40 clears the the top wall 104 of the temperature controlled chamber 36 so that the stem 72 is fully visible to an operator for performing remedial action. From block 174, operation proceeds to block 176 wherein the operator is signaled to take remedial action.

During normal operation of the system 20, the tip 70 is present on the stem 72 and, accordingly, at block 172 the safety level would not be reached without interruption of the light beam 114. Accordingly, operation proceeds from block 172 along line 178 back to block 166 wherein the microprocessor 62 continues to lower the pipette at the preset rate. The operation continues in repetitive fashion through the blocks 166, 168, and 170 until interruption of the light beam 114 occurs at line 180. The interruption of the light beam 114 is signaled to the microprocessor 62 by a change in the output signal of the comparison circuitry 118 such that the signal changes from logic-1 to logic-0.

Assuming that the tip 70 is present, then, upon the interruption of the light beam at line 180, the output signal of the comparison circuitry 118 is at logic-0 to indicate to the microprocessor 62 that the tip 70 is present, and that the tip 70 has reached the position of the light beam 114 along the path of travel of the tip 70 towards the cartridge 22. Accordingly, at block 182, the microprocessor 62 determines the position of the dispense level (FIG. 7) so as to compute the additional amount of travel required by the tip 70 to reach the dispense level. The operation within block 182 will be described in further detail with reference to FIG. 6.

In FIG. 5, the operation proceeds from block 182 via line 186 to block 188 wherein the pipette 40 is lowered further to locate the tip 70 at the dispense level. This lowering of the pipette is accomplished, in the manner disclosed hereinabove with reference to the feedback circuit 142 of FIG. 4, wherein the microprocessor 62 inputs further locations along the travel path of the pipette to bring the tip 70 to the dispense level. Thereafter, at block 190 the microprocessor 62 commands the suction control unit 128 to dispense liquid to the selected compartment 106 of the cartridge 22. Thereafter at block 192, the pipette 40 is retracted back from the cartridge 22 to the transport level. The instrument 20 can now initiate other steps in the testing procedures of the cartridges 22.

FIG. 6 shows details in the procedure of block 182 (FIG. 5) for checking the presence of the pipette tip followed by the computation of the additional travel of the pipette. The procedure at line 180 proceeds to block 194 to check the intensity of the light beam. In the event that, at block 194, the light is fully obscured, the signal of the comparison circuit 118 is at logic-0, as was noted hereinabove, which allows the microprocessor 62 to determine, at block 198, that the pipette is present. Thereupon, at block 200 the microprocessor reads the present pipette position as outputted by the encoder 152 (FIG. 4). This is followed, at block 202, by a reading of the position data of the cartridge 22, which data has been stored in the memory 154 (FIG. 4).

The cartridge position data designates the location of a top surface of the cartridge 22 relative to the top surface 158 of the carousel 24. Since the distance between the light beam 114 and the carousel surface 158 is known and fixed, the inputting of this cartridge data is equivalent to giving the microprocessor the distance between the top surface of the cartridge 22 and the beam 114. Accordingly, at block 204, the additional distance between the beam 114 and the cartridge 22 is added to the vertical distance already traveled by the pipette 40, the vertical distance being provided by the encoder 152. This gives the reading of the encoder 152 which will be obtained when the pipette tip 70 reaches the dispense level. This information is used by the microprocessor 62 in operating the circuit of FIG. 4 for continued lowering of the pipette 40. Accordingly, the operation can now proceed via line 186 to block 188 as has been disclosed above with reference to FIG. 5.

The timing diagram of FIG. 7 has already been referred to in the description of the circuitry of FIG. 4 and the procedure of FIGS. 5 and 6. Briefly, the diagram of FIG. 7 shows the descent of the pipette tip 70 at a fixed rate during the initial descent interval during which the condition of the light beam is observed, followed by the final descent in which the pipette tip 70 is brought to the dispense level. At the conclusion of the dispense interval, the tip 70 is retracted to the transport level. The safety level is disposed between the light beam level and the dispense level.

The foregoing description provides for operation of the test system 20 in a fashion which allows the pipette to be lowered with an accuracy which is independent of the position of the pipette tip 70 on the pipette stem 72.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. A method for dispensing fluid to an assay element in an analytical instrument including a pipette, the instrument comprising transport means for advancing the pipette between s reservoir holding a fluid, the assay element and a supply of disposable pipette tips adapted to be affixed to a stem of the pipette, the method comprising:
   (a) affixing a tip on the stem and aspirating fluid into said tip;
   (b) advancing the pipette along a predetermined path toward an assay element carried on a conveyor;
   (c) designating a reference location on said path by means of a light beam which is located a predetermined distance from said conveyor;
   (d) observing a breaking of the light beam by the tip during a movement of the pipette along the path, the breaking of the light beam signaling a position of said tip at said reference location;
   (e) computing an additional increment of travel based on the height of said assay element above a reference surface of said conveyor; and
   (f) advancing the pipette said additional increment of travel from said reference location toward the assay element prior to dispensing the fluid to the assay element.

2. A method according to claim 1 further comprising a step of:
   setting a second reference location beyond said first mentioned reference section along said path of travel; and
   wherein, upon a failure to observe the breaking of the light beam in said observing step (d), said advancing step (b) is continued until said pipette reaches said second reference location.

3. A method according to claim further comprising the steps of:
   dispensing the fluid to said assay element; and
   retracting said pipette from said assay element.

4. A method according to claim 1 wherein said step of observing includes measuring the intensity of said light beam, a fully obscured light beam indicating that said pipette tip is present.

5. A method according to claim 2 further comprising the steps of retracting said pipette and signaling a fault in the test system.

6. An analytical instrument in combination with a reservoir storing a fluid and employing a pipette for dispensing the fluid to an assay element, the instrument comprising:
   a pipette and a supply of disposable pipette tips to be affixed to a stem of the pipette;
   a conveyor for carrying an assay element;
   transport means for advancing the pipette to said supply of disposable pipette tips for replenishment of a tip, the transport means advancing the pipette between the reservoir and an assay element for dispensing the fluid; and
   wherein the analytical instrument further comprises an optical detection system which provides a light beam at a predetermined position relative to said conveyor for sensing the location of said pipette tip, the detection system providing a location signal indicating the presence of said tip at a reference location on a path of travel of the tip toward an assay element, the reference location being distant from the assay element; and
   said transport means moving said pipette to the reference location, said instrument including means responsive to the location signal for computing an additional distance of travel based on the height of an assay element above a reference surface of said conveyor and for advancing said pipette tip from said reference location by said additional distance for placing said tip in a position for dispensing the fluid to an assay element.

7. An analytical instrument according to claim 6 wherein
   said transport means in moving said pipette beyond said reference location to a second reference location on said travel path in the absence of an interruption of said light beam; and
   said means responsive to said location signal is further responsive to the location of said pipette on said travel path for signaling the absence of said tip on said stem upon the attainment of said second reference location by said pipette without interruption of said light beam.

* * * * *

UNITED STATES PATENT AND TRADEMARK OFFICE
CERTIFICATE OF CORRECTION

PATENT NO. : 5,141,871
DATED : August 25, 1992
INVENTOR(S) : Fareed Kureshy, et. al.

It is certified that error appears in the above-indentified patent and that said Letters Patent is hereby corrected as shown below:

On the Title page, item [57], Abstract, line 1, "isntrument" should be --instrument--.

Column 5, line 32, "two" should be --a--.

Column 6, line 52, "With" should be --with--.

Column 11, line 32, "s" should be --a--.

Column 11, line 57, "section" should be --location--.

Column 12, line 5, after "claim" insert --1--.

Column 12, line 48, delete "in".

Signed and Sealed this

Seventh Day of September, 1993

Attest:

BRUCE LEHMAN

Attesting Officer     Commissioner of Patents and Trademarks